US010124108B2

(12) United States Patent
Stefani et al.

(10) Patent No.: US 10,124,108 B2
(45) Date of Patent: Nov. 13, 2018

(54) APPARATUS FOR EXTRACORPOREAL BLOOD TREATMENT AND A RELATED CONTROL METHOD (71) Applicant: GAMBRO LUNDIA AB, Lund (SE)

(72) Inventors: David Stefani, Modena (IT); Mariano Ruffo, Modena (IT)

(73) Assignee: GAMBRO LUNDIA AB, Lund (SE)

( * ) Notice: Subject to any disclaimer, the term of this patent is extended or adjusted under 35 U.S.C. 154(b) by 380 days.

(21) Appl. No.: 14/903,478

(22) PCT Filed: Jul. 4, 2014

(86) PCT No.: PCT/EP2014/064357
§ 371 (c)(1),
(2) Date: Jan. 7, 2016

(87) PCT Pub. No.: WO2015/004030
PCT Pub. Date: Jan. 15, 2015

(65) Prior Publication Data
US 2016/0144096 A1  May 26, 2016

(30) Foreign Application Priority Data
Jul. 10, 2013 (EP) .................................... 13175841

(51) Int. Cl.
A61M 1/36 (2006.01)
A61B 5/00 (2006.01)
(Continued)

(52) U.S. Cl.
CPC ....... A61M 1/3639 (2013.01); A61B 5/02141 (2013.01); A61B 5/4836 (2013.01);
(Continued)

(58) Field of Classification Search
CPC ..... A61B 5/02141; A61B 5/08; A61B 5/4836; A61B 5/6866; A61M 1/16; A61M 1/267;
(Continued)

(56) References Cited

U.S. PATENT DOCUMENTS

2011/0301472 A1* 12/2011 Grober .................. A61B 5/021
600/485
2013/0172803 A1* 7/2013 Olde .................... A61B 5/0215
604/6.11
2014/0231319 A1* 8/2014 Olde .................. A61B 5/02108
210/97

FOREIGN PATENT DOCUMENTS

DE       100 33 192        1/2002
GB       1212764 A  *  11/1970  .............. B60T 8/172
(Continued)

OTHER PUBLICATIONS

International Search Report; PCT/EP2014/064357; dated Sep. 23, 2014; 4 pages.
(Continued)

Primary Examiner — Benjamin Klein
(74) Attorney, Agent, or Firm — K&L Gates LLP (57) ABSTRACT An apparatus for extracorporeal blood treatment (1) is described, comprising a treatment unit (3) having at least a first chamber (4) and at least a second chamber (5) separated from one another by a semi-permeable membrane (6); at least a blood removal line (7) connected to an inlet port (4a) of the first chamber (4) and predisposed to remove blood from a patient (P); at least a blood return line (8) connected to an outlet port (4b) from the first chamber (4) and predisposed to return treated blood to the patient (P), wherein the blood removal line (7), the blood return line (8) and the first chamber (4) are part of an extracorporeal blood circuit (2); at least a peristaltic pump (9) operating at the extracorporeal blood circuit (2) for moving the blood in the
(Continued)

circuit; at least a pressure sensor (13, 14) associated to the extracorporeal blood circuit (2) and configured to enable determining pressure values in the extracorporeal blood circuit (2); at least a fluid drainage line (23) connected to an outlet port of the second chamber (5); a control unit (CU) connected to the at least a pressure sensor (13, 14) and to the peristaltic pump (9) and configured to: move the peristaltic pump (9) with a cyclic motion to generate a blood flow; receive from the at least a pressure sensor (13, 14) a signal (Ps) indicating the pressure of the blood in the extracorporeal blood circuit (2). The signal (Ps) indicating the blood pressure is detected with a time do main frequency depending on the velocity.

35 Claims, 3 Drawing Sheets

(51) Int. Cl.
    *A61B 5/021*      (2006.01)
    *A61M 1/26*       (2006.01)
    *A61M 1/16*       (2006.01)
    *A61B 5/08*       (2006.01)

(52) U.S. Cl.
    CPC ........... *A61B 5/6866* (2013.01); *A61M 1/267* (2014.02); *A61M 1/36* (2013.01); *A61M 1/3607* (2014.02); *A61M 1/3653* (2013.01); *A61M 1/3656* (2014.02); *A61B 5/08* (2013.01); *A61M 1/16* (2013.01); *A61M 2205/3331* (2013.01); *A61M 2205/3344* (2013.01); *A61M 2205/3365* (2013.01); *A61M 2205/52* (2013.01)

(58) Field of Classification Search
    CPC .... A61M 1/36; A61M 1/3607; A61M 1/3639; A61M 1/3653; A61M 1/3656; A61M 2205/3331; A61M 2205/3334; A61M 2205/3365; A61M 2205/52
    See application file for complete search history.

(56) References Cited

FOREIGN PATENT DOCUMENTS

| | | |
|---|---|---|
| WO | 03002174 | 1/2003 |
| WO | 2008006559 | 1/2008 |
| WO | 2012175267 | 12/2012 |
| WO | 2013000777 | 1/2013 |

OTHER PUBLICATIONS

Written Opinion; PCT/EP2014/064357; dated Sep. 23, 2014; 6 pages.

* cited by examiner

APPARATUS FOR EXTRACORPOREAL BLOOD TREATMENT AND A RELATED CONTROL METHOD

CROSS-REFERENCE TO RELATED APPLICATIONS

The present application is a National Phase of International Application No. PCT/EP2014/064357, filed on Jul. 4, 2014, which claims priority to Europe Patent Application No. 13175841.9, filed Jul. 10, 2013, the entire contents of each of which are incorporated herein by reference and relied upon.

FIELD OF INVENTION

The present invention relates to an apparatus for extracorporeal blood treatment and also to a related control method of the apparatus.

BACKGROUND OF INVENTION

The known extracorporeal blood treatment apparatus comprise at least a treatment unit (for example a dialyser or filter or an ultrafilter or a plasma filter or a filter unit of a different type) having a semi-permeable membrane which separates the treatment unit into two chambers. An extracorporeal blood circuit enables circulation of blood taken from a patient within the first chamber. At the same time, and typically in a counter-current direction with respect to the blood, a treatment fluid is circulated across a special circuit in the second chamber of the treatment unit. A blood removal line is connected with an inlet port of the first chamber and is predisposed, in operating conditions of connection to a patient, to remove blood from a vascular access inserted, for example, in a fistula on the patient. A blood return line connected with an outlet port of the first chamber is predisposed to receive the blood treated by the treatment unit and to return the treated blood to a further vascular access connected to the patient's fistula. A peristaltic pump operatively coupled to the extracorporeal blood circuit circulates the blood in the circuit. This type of blood treatment apparatus, known as dialysis apparatus, can be used for removal of solutes and excess fluid from the patient's blood where the patient is suffering from kidney failure.

During this treatment it is necessary to monitor and analyse the behaviour of the patient's physiological pressure generators, such as the heart and/or the breathing system. For example, to monitor the heartbeat of a subject, the blood pressure and also the state of the vascular accesses (for example to identify the dislodgement of the venous needle VND), it is advisable to extract/isolate the pressure data deriving from the physiological pressure generators. To this end the pressure signals detected by special sensors arranged in the extracorporeal blood circuit must be treated/filtered in order to remove noise.

The Applicant has observed that the existing and known solutions operating the treatment/filtering operations require large memory capacity and computational power in order to process the pressure signals in the most efficient way with the aim of guaranteeing the correct functioning of the apparatus and the respect of the treatment parameters of the patient.

In particular, the Applicant has observed that the performance of the algorithms at the base of the treatment of pressure signals is negatively influenced by the fact that the sampling frequency of the pressure signals is constant so that the samples acquired in a rotation of the pump decrease as the rotation velocity of the pump increases, and vice versa.

SUMMARY

In this context, an aim of the present invention is to provide a blood treatment apparatus able to monitor and analyse the behaviour of physiological pressure generators of the patient in a correct and functional way.

A particular aim of the present invention is to provide an apparatus that is able to efficiently extract/isolate the pressure data deriving from the physiological pressure generator.

A further aim of the present invention is to provide an apparatus able to carry out processing of the pressure data in a simple way, i.e. without excessive computational effort, and thus also reliably.

A further aim of the present invention is to provide an apparatus able to carry out the data processing operations with simple and economical hardware and software.

A further aim of the present invention is to provide an apparatus able to carry out data processing operations requiring only a minimum updating of the hardware and software with respect to those already present in existing apparatus.

At least one of the above-indicated aims is substantially attained by a blood treatment apparatus according to one or more of the accompanying claims.

Aspects of the invention are illustrated in the following.

In an independent first aspect of the invention, an apparatus is described for extracorporeal blood treatment comprising:
  at least a treatment unit (3) having at least a first chamber (4) and at least a second chamber (5) separated from one another by a semi-permeable membrane (6);
  at least a blood removal line (7) connected to an inlet port (4a) of the first chamber (4) and predisposed to remove blood from a patient (P);
  at least a blood return line (8) connected to an outlet port (4b) from the first chamber (4) and predisposed to return treated blood to the patient (P), wherein the blood removal line (7), the blood return line (8) and the first chamber (4) are part of an extracorporeal blood circuit (2);
  at least a peristaltic pump (9) operating at the extracorporeal blood circuit (2) for moving the blood in the circuit (2);
  at least a pressure sensor (13, 14) associated to the extracorporeal blood circuit (2) and configured to enable determination of pressure values in said extracorporeal blood circuit (2);
  at least a fluid drainage line (23) connected to an outlet port of said second chamber (5);
  a control unit (CU) connected to said at least a pressure sensor (13, 14) and to the peristaltic pump (9) and configured to:
    move the peristaltic pump (9) with a cyclic motion to generate a blood flow;
    receive from said at least a pressure sensor (13, 14) a signal (Ps) indicating the pressure of the blood in the extracorporeal blood circuit (2);
    sample, for each cycle of the peristaltic pump (9), the signal (Pr) indicating the blood pressure with a frequency in the time domain depending on the velocity ($\omega$) of the peristaltic pump (9).

In a second aspect of the invention a sampling method of pressure signals in extracorporeal blood treatment apparatus is provided, the apparatus comprising:

at least a treatment unit (3) having at least a first chamber (4) and at least a second chamber (5) separated from one another by a semi-permeable membrane (6);

at least a blood removal line (7) connected to an inlet port (4a) of the first chamber (4) and predisposed to remove blood from a patient (P);

at least a blood return line (8) connected to an outlet port (4b) from the first chamber (4) and predisposed to return treated blood to the patient (P), wherein the blood removal line (7), the blood return line (8) and the first chamber (4) are part of an extracorporeal blood circuit (2);

at least a peristaltic pump (9) operating at the extracorporeal blood circuit (2) for moving the blood in the circuit (2);

at least a pressure sensor (13, 14) associated to the extracorporeal blood circuit (2) and configured to enable determination of pressure values in the extracorporeal blood circuit (2);

at least a fluid drainage line (23) connected to an outlet port of the second chamber (5);

wherein the method comprises:

moving the peristaltic pump (9) with a cyclic motion to generate a blood flow;

receiving from said at least a pressure sensor (13, 14) a signal (Ps) indicating the pressure of the blood in the extracorporeal blood circuit (2);

sampling, for each cycle of the peristaltic pump (9), the signal (Ps) indicating the blood pressure with a frequency in the time domain depending on the velocity ($\omega$) of the peristaltic pump (9).

In an aspect, the signal (Pr) indicating the blood pressure is detected when the peristaltic pump (9) is in a plurality of predefined positions ($pp_1$-$pp_y$).

In other words, the detecting instants of the pressure signal coincide with the passage of the peristaltic blood pump through a plurality of predefined positions ($pp_1$-$pp_y$) during the cyclic motion thereof.

Therefore, as the velocity ($\omega$) of the pump (9) is not constant, the sampling of the pressure signal (or signals) is carried out with a variable frequency over time since it depends on the velocity of the peristaltic blood pump (9).

From another point of view according to the invention, the pressure signal is sampled at a constant frequency in the spatial domain (constant for each pump cycle) while previously (known art) the sampling of the data was done at a constant frequency in the time domain.

In the invention, the number of samples acquired in a rotation of the pump is constant and does not depend on the actual rotating velocity of the pump.

In this way the sampling takes account of the state of the blood circuit which also depends on the position of the peristaltic blood pump and the velocity thereof.

In a 3rd aspect according to any one of the preceding aspects, the predefined positions ($pp_1$-$pp_y$) are spatially equidistant. The cyclic pathway the peristaltic pump follows is sub-divided by the predefined positions ($pp_1$-$pp_y$) in linear or angular spatial intervals of equal entity.

In a 4th aspect according to any one of the preceding aspects, the predefined positions are in a number "y" where "y" is greater than or equal to fifty, for instance greater than one hundred, for instance equal to one hundred and twenty.

This number is sufficient to ensure a sampling frequency (variable over time) to correctly represent the progression of the pressure signal.

In a 5h aspect according to any one of the preceding aspects, the apparatus comprises at least a position sensor (32) associated to the peristaltic pump (9) and configured to determine positions of the peristaltic pump (9);

wherein the control unit (CU) is configured to carry out the sampling step which comprises:

receiving from the position sensor (32) a succession of "n" reference signals ($sr_1$-$sr_n$) indicating reference positions ($pr_1$-$pr_n$) of the peristaltic pump (9);

determining the signal (Ps) indicating the blood pressure every "m" reference signals ($sr_1$-$sr_n$), where "m" is equal to or greater than one and less than or equal to "n".

In other words, the reference signals ($sr_1$-$sr_n$) generated in a pump cycle can all be used to command detection of the signal (Ps) indicating the pressure or only one every "m". The "n/m" ratio is therefore equal to "y". If all are used, the reference positions are predefined positions, otherwise only a part of the reference positions are predefined positions.

In a 6th aspect according to the fifth aspect, "n" is greater than or equal to fifty, for instance greater than or equal to five hundred, for instance equal to nine hundred and sixty.

In a 7th aspect according to the fifth or sixth aspect, "m" is smaller than ten, for instance equal to eight.

If the "n" reference signals are nine hundred and sixty and "m" is eight, the signal (Ps) indicating the blood pressure is sampled one hundred and twenty times (the number "y" of predefined positions) for each cycle of the peristaltic pump.

In an 8th aspect according to any one of the preceding aspects, the peristaltic pump (9) is a rotary pump. The predefined positions ($p_1$-$p_y$) are angular positions of the peristaltic pump.

In a 9th aspect according to any one of aspects from 1 to 7, the peristaltic pump (9) is of a linear type. This type of pump comprises a plurality of pumping elements (arms arranged and actuated sequentially such as to engage and squeeze successive portions of tube which the pump engages) or possibly other actuators able to generate a pulsating motion in the blood, i.e. a non-constant flow that oscillates about a mean flow value. The predefined positions ($p_1$-$p_y$) are linear positions of the peristaltic pump.

In a 10th aspect according to any one of aspects from one to eight, the position sensor (32) comprises a phonic wheel coupled to the peristaltic pump (9).

In an 11th aspect according to the tenth aspect, a rotor (34) of the phonic wheel (32) rotates, for instance solidly, with the peristaltic pump (9). A pickup (34) of the phonic wheel (32) is fixed with respect to a frame of the apparatus (1) and moves with respect to the pump (9) and the rotor (33).

In a 12th aspect according to the tenth aspect, a rotor (34) of the phonic wheel (32) is fixed and a pickup (34) is mounted on the rotary pump (9).

According to both the eleventh and twelfth aspects, the rotor (33) of the phonic wheel (32) bears "n" signs ($r_1$-$r_n$) corresponding to the "n" reference signals ($sr_1$-$sr_n$). This is a very simple and effective system for detecting the angular position of the peristaltic pump and, possibly, also the angular velocity thereof.

In a 13th aspect according to aspects 10, 11 or 12, the phonic wheel (32) is of the inductive type. The rotor (33) exhibits a plurality of prominences or teeth ("n" signs ($r_1$-$r_n$)) made of a ferromagnetic material and a proximity sensor (34, pickup) facing the rotor (33) detects the flow variation in the magnetic field due to the passage of the prominences. The flow variation creates an induced alternating pulsating current and each pulse corresponds to a prominence.

In a 14th aspect according to aspects 10, 11 or 12, the phonic wheel (32) is capacitive. The rotor exhibits a plurality of prominences or teeth ("n" signs ($r_1$-$r_n$)) connected to an electric line and the sensor (pickup) is a contact pole touched by the rotating teeth. Each tooth corresponds to an instantaneous closing of the circuit, with a consequent electric pulse, followed immediately by the re-opening of the contact.

In a 15th aspect according to aspects 10, 11, or 12, the phonic wheel (32) is of an optic type. The rotor comprises sectors of opaque material alternated with sectors of reflective material ("n" signs ($r_1$-$r_n$)). A laser strikes the rotor and a return sensor (pickup) detects the reflected laser beam from the rotor. The opaque material completely absorbs the laser while the reflective material returns it as a reflection, and a signal corresponds to each passage from opaque to reflective.

The control unit (CU) receives, from the pickup (34), the succession of "n" reference signals ($sr_1$-$sr_n$) and samples the signal (Ps) indicating the blood pressure every "m" reference signals, where "m" is equal to or greater than one. In other words, not all the "n" reference signals ($sr_1$-$sr_n$) of the phonic wheel (32) are used as commands for detecting the pressure signal, but only one every "m".

In a 16th aspect according to any one of the preceding aspects, the control unit (CU) is configured to:
receive a signal ($\omega$, Fr) indicating the instant blood flow (Qb) in the peristaltic pump (9);
compare the signal ($\omega$, Fr) with a plurality of fields ($\Delta\omega_1$-$\Delta\omega_j$, $\Delta Fr_1$-$\Delta Fr_j$) indicating predefined intervals of blood flow ($\Delta Qb_1$-$\Delta Qb_j$) each combined with a respective predefined sampling frequency ($Fs_1$-$Fs_j$) of the signal (Ps) indicating the blood pressure;
identify the field ($\Delta\omega_k$, $\Delta Fs_k$) in the plurality of fields ($\Delta Fr_1$-$\Delta Fr_j$) to which the signal belongs ($\omega$, Fr);
identify the respective predefined sampling frequency ($Fs_k$);
dimension a filter to be used on the basis of the predefined sampling frequency ($Fs_k$) and at a desired cutting frequency (Fc);
apply the filter to the sampled signal (Ps) indicative of the blood pressure.

In accordance with the instant value measured by the blood flow "Qb", the control unit "CU" uses one of the filters and changes the filter when the instant value measured by the blood flow "Qb" during the treatment falls within a different interval.

In a 17th aspect according to the 16th aspect, the signal ($\omega$, Fr) indicating the instant blood flow (Qb) is a cyclic velocity ($\omega$), for instance angular, of the peristaltic pump (9).

In an 18th aspect according to the 17th aspect, the cyclic velocity ($\omega$) is calculated through the phonic wheel (32).

In a 19th aspect according to the 17th aspect, ($\omega$) is detected through a device distinct from the phonic wheel, for example a Hall-effect sensor which detects the passage of lobes (15) of the pump (9).

In a 20th aspect according to the 17th, 18th or 19th aspect, the cyclic velocity ($\omega$) is an average calculated on each cycle of the peristaltic pump (9).

In a 21st aspect according to the 20th aspect, the cyclic velocity ($\omega$) is calculated by:
supplying a first counter with the "n" reference signals of the phonic wheel (32) corresponding to a 360° rotation;
increasing a second time counter (for instance every 2 ms) until the first counter reaches the n-th signal;
considering the inverse of the time used to perform the rotation (time-cycle $\Delta T$ given by the second counter) for obtaining the cyclic velocity ($\omega$) in [cycles/s].

In a 22nd aspect according to aspects 17, 18, 19 or 20, 21, the fields ($\Delta\omega_1$-$\Delta\omega_j$, $\Delta Fr_1$-$\Delta Fr_j$) indicating the predefined blood flow ($\Delta Qb_1$-$\Delta Qb_j$) are cyclic velocity fields ($\Delta\omega_1$-$\Delta\omega_j$), for instance angular velocity fields.

Given the volume of blood (Sv) moved by the peristaltic pump in a complete cycle in [ml/cycle] and given the velocity ($\omega$) of the peristaltic pump in [cycle/s] the flow (Qb) of the peristaltic pump in [ml/min] is given by the relation: Qb=$\omega$×Sv×60.

The predefined sampling frequency ($Fs_k$) is the one associated to the field ($\Delta\omega_k$) among the cyclic velocity fields ($\Delta\omega_1$-$\Delta\omega_j$) in which the detected cyclic velocity ($\omega$), corresponding to the instant blood flow (Qb), falls.

In a 23rd aspect according to the 16th aspect, the signal ($\omega$, Fr) indicating the instant blood flow (Qb) is a frequency (Fr) of reference signals ($sr_1$-$sr_n$) indicating positions of the peristaltic pump (9).

In a 24th aspect according to the 23rd aspect, the frequency (Fr) of the reference signals ($sr_1$-$sr_n$) is an average calculated on each cycle of the peristaltic pump (9).

In a 25th aspect according to aspects 23 or 24, the fields ($\Delta\omega_1$-$\Delta\omega_j$, $\Delta Fr_1$-$\Delta Fr_j$) indicating the predefined blood flow intervals ($\Delta Qb_1$-$\Delta Qb_j$) are frequency fields ($\Delta Fr_1$-$\Delta F_n$) of reference signals ($sr_1$-$sr_n$) indicating positions of the peristaltic pump, Given the volume of blood (Sv) moved by the peristaltic pump (9) in a complete cycle in [ml/cycle], given the frequency (Fr) of the reference signals (n') indicating the positions of the peristaltic pump (9) in [1/s] and given the number of the reference signals (n, acquired points) in a complete cycle of the peristaltic pump (9), the flow (Qb) of the peristaltic pump (9) in [ml/min] is given by the relation: Qb=Fr×(Sv×60)/n'.

The predefined sampling frequency ($Fs_k$) is the one associated with that field ($\Delta Fr_k$), among the frequency fields ($\Delta Fr_1$-$\Delta Fr_1$) of the reference signals ($sr_1$-$sr_n$), in which the detected frequency (Fr) of the reference signals ($sr_1$-$sr_n$), corresponding to the instant blood flow (Qb), falls.

In a 26th aspect according to aspects 23 and/or 24 and/or 25, the frequency (Fr) of the reference signals ($sr_1$-$sr_n$) corresponds to the sampling frequency (Fs) of the signal (Ps) indicating the blood pressure. In this case the reference signals (n') taken into consideration between the (n) reference signals are only those of the predefined positions (y) of the peristaltic pump (n'=y). Given the number of the predefined positions (y) and the time-cycle ($\Delta T$) of the peristaltic pump, the frequency (Fr) of the reference signals is given by the relation: Fr=Fs=y/$\Delta T$.

In a 27th aspect according to aspects 23 and/or 24 and/or 25, the frequency (Fr) of the reference signals ($sr_1$-$sr_n$) corresponds to a multiple of the sampling frequency (Fs) of the signal (Ps) indicating the blood pressure. In this case, the reference signals (n') taken into consideration among the (n) reference signals are all those (n) reference signals or a multiple (X) of those corresponding to the predefined positions (y) of the peristaltic pump (n'=X×n). For example, considering all the (n) reference signals and the time-cycle ($\Delta T$) of the peristaltic pump, the frequency (Fr) of the reference signals is given by the relation: Fr=n/$\Delta T$ where n=m×y so that Fr=m×Fs.

In a 28th aspect according to aspects 26 or 27, the frequency (Fr) of the reference signals ($sr_1$-$sr_n$) is calculated by:

supplying a first counter with the (n') reference signals taken into consideration among the (n) reference signals ($sr_1$-$sr_n$) corresponding to a rotation of 360°;

increasing a second time counter (for instance every 2 ms) until the first counter reaches the n'-th signal;

dividing the number (n') of reference signals ($sr_1$-$sr_n$) taken into consideration for the time-cycle ΔT (given by the second counter) for obtaining the frequency (Fr) in [1/s].

In a 29th aspect according to one or more of aspects from 16 to 28, each predefined sampling frequency ($Fs_1$-$Fs_j$) corresponds to a predefined value ($Qb_1$-$Qb_j$) of the respective predefined blood flow interval ($ΔQb_1$-$ΔQb_j$).

In an aspect, the predefined value ($Qb_1$-$Qb_j$) is a median value of the respective predefined blood flow interval ($ΔQb_1$-$ΔQb_j$).

Using the predefined value ($Qb_1$-$Qb_j$) of each of the flow intervals ($ΔQb_1$-$ΔQb_j$), a calculation is made of one of the predefined sampling frequency values ($Fs_1$-$Fs_j$) using the formula:

$$Fs = Qb \times (y/Sv \times 60)$$

where (Sv) is the blood volume moved by the peristaltic pump in a complete cycle in [ml/cycle] and (y) is the number of predefined positions.

To each predefined value ($Qb_1$-$Qb_j$) of each of the flow intervals ($ΔQb_1$-$ΔQb_j$) corresponds a predefined cyclic velocity value ($ω_1$-$ω_j$) of each of the cyclic velocity fields ($Δω_1$-$Δω_j$) and a predefined frequency value ($Fr_1$-$Fr_j$) of the reference signals of the frequency fields ($ΔFr_1$-$ΔFr_j$) of the reference signals ($sr_1$-$sr_n$).

In a 30th aspect according to the 29th aspect, the predetermined sampling frequency values ($Fs_1$-$Fs_j$) can be calculated directly by the predefined values (median) of cyclic velocity ($ω_1$-$ω_j$) using the relation:

$$Fs = ω \times y$$

or by the predefined values (median) of frequency ($Fr_1$-$Fr_j$) of the reference signals with the relation:

$$Fs = Fr \times y/n$$

If the frequency (Fr) of the reference signals is the sampling frequency (Fs) of the signal (Ps) indicating the blood pressure, then the predefined values (median) of frequency ($Fr_1$-$Fr_j$) of the reference signals are the predefined sampling frequency value ($Fs_1$-$Fs_j$).

In a 31st aspect according to one or more of the aspects from 16 to 30, the number (j) of predefined intervals of blood flow ($ΔQb_1$-$ΔQb_j$) is comprised between two and five, for instance either three or four. To each of the intervals ($ΔQb_1$-$ΔQb_j$) corresponds a predefined sampling frequency ($Fs_1$-$Fs_j$). By containing the number of intervals/frequency of sampling, the computational weight is reduced for the calculation of the filters. This choice is an excellent compromise between simplicity of calculation and uncertainty of the determination of the filters.

In a 32nd aspect according to one or more of aspects from 16 to 31, the predefined blood flow intervals ($ΔQb_1$-$ΔQb_j$) are comprised between about 0 ml/min and about 600 ml/min, for instance between about 10 ml/min and circa 580 ml/min.

In a 33rd aspect according to aspects 31 or 32, the predefined blood flow intervals (ΔQb1-ΔQbj) are the following: ΔQb1=10-265 ml/min, ΔQb2=265-335 ml/min, ΔQb3=335-580 ml/min.

In a 34th aspect each filter combined to a predefined sampling frequency ($Fs_1$-$Fs_j$) is defined as follows:

calculating the cutting frequency "wc" expressed in radians as $ω_c = 2π \times Fc/Fs$;

expressing the pulse response which characterizes the low-pass filter according to the cutting frequency "$ω_c$" as:

$$h_{lp}[n] = \frac{1}{2π} \int_{-ω_c}^{ω_c} e^{jωn} dω$$

$$= \frac{1}{2π jn} [e^{jωn}]_{-ω_c}^{ω_c} = \frac{1}{2π jn}(e^{jω_c n} - e^{-jω_c n})$$

$$= \frac{\sin ω_c n}{π n}, -∞ < n < ∞$$

In a 35th aspect according to one or more of aspects from 16 to 34, the desired cutting frequency "Fc" is comprised between about 1 Hz and about 4 Hz, for instance 2 Hz.

In a 36th aspect according to one or more of aspects from 16 to 35, the filters are applied to the signal "Ps" indicating the blood pressure in the extracorporeal blood circuit (2) to extract/isolate the pressure data deriving from the physiological pressure generators with the aim, for example, of monitoring the venous access (VNM), and of identifying the so-called venous needle dislodgement (VND).

DESCRIPTION OF THE DRAWINGS

Some drawings relating to aspects of the invention are provided by way of non-limiting example.

In particular.

DETAILED DESCRIPTION

With reference to the accompanying drawings, 1 denotes an apparatus for extracorporeal blood treatment.

The apparatus 1 comprises an extracorporeal circuit 2 intended to extract blood to be processed from the cardiovascular system of a patient "P" and to return the treated blood to the patient.

In the following passages some possible examples of the general structure of the apparatus 1 are described. In particular, some configurations of the extracorporeal blood circuit 2, of any possible infusion lines in which a replacement fluid circulates, of the dialysis line, if any, in which a dialysis fluid circulates, and of the discharge line of the discharge fluid are described below.

Figure 1:
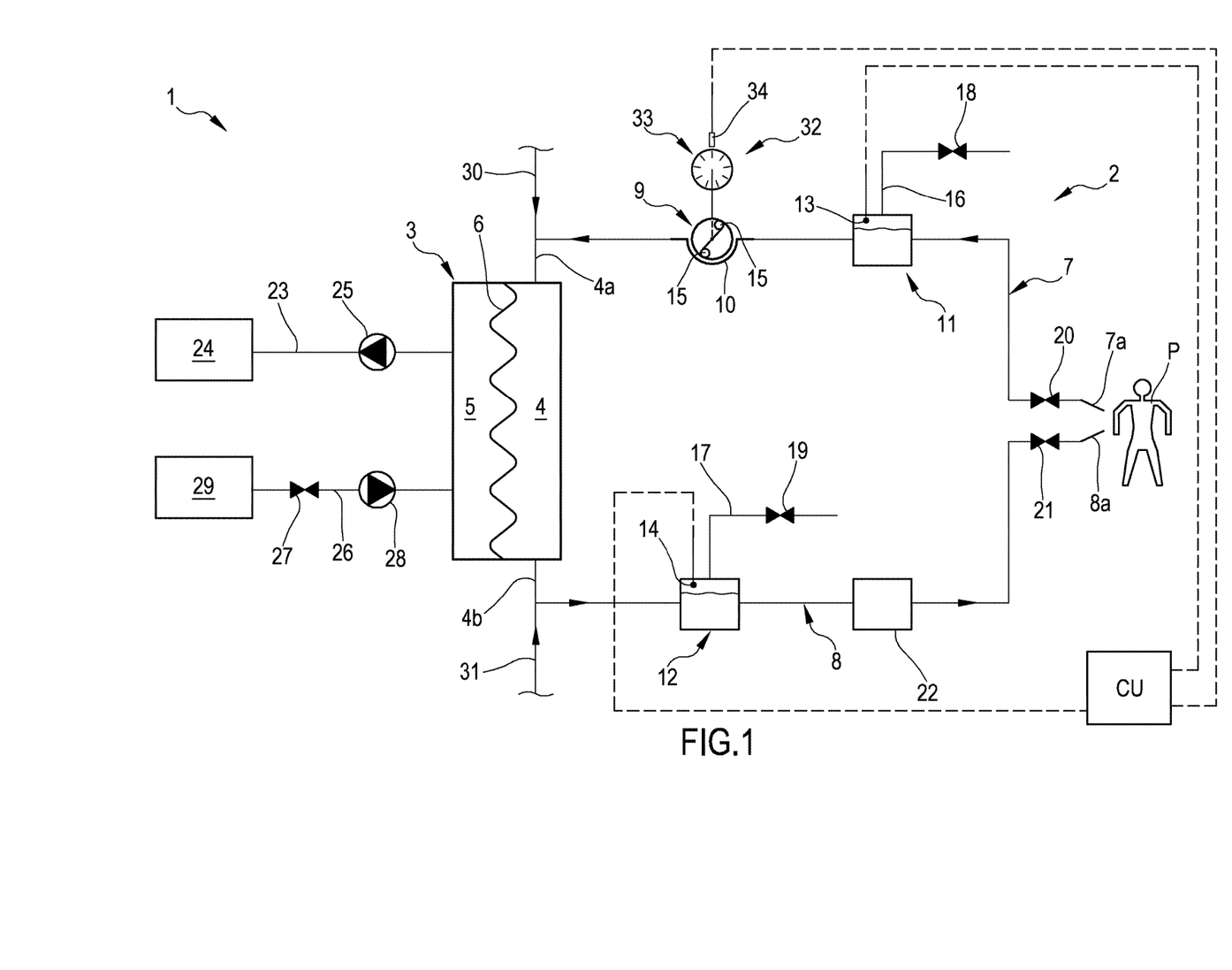
FIG. 1 schematically shows a blood treatment apparatus according to the invention.

With reference to FIG. 1, the apparatus 1 for extracorporeal blood treatment comprises at least a treatment unit 3, for example a hemofilter, a hemodiafilter, a plasma filter, a dialysis filter, a membrane oxygenator or another unit intended to process the blood removed from the patient, having at least a first chamber and at least a second chamber 4 and 5 separated from one another by a semipermeable membrane 6. A blood removal line 7 is connected by an inlet port 4a to the first chamber 4 and is predisposed, in operating positions of connection to the patient "P", to remove blood from a vascular access inserted, for example, in a fistula in the patient "P". A blood return line 8 connected with an outlet port 4b of the first chamber 4 is designed to receive the treated blood from the treatment unit 3 and to return the treated blood to a further vascular access connected with the fistula of the patient "P". Note that the configuration of the vascular access can be of any type: for example a catheter, a port implanted in the patient, a cannula, a needle etc.

Figure 2:
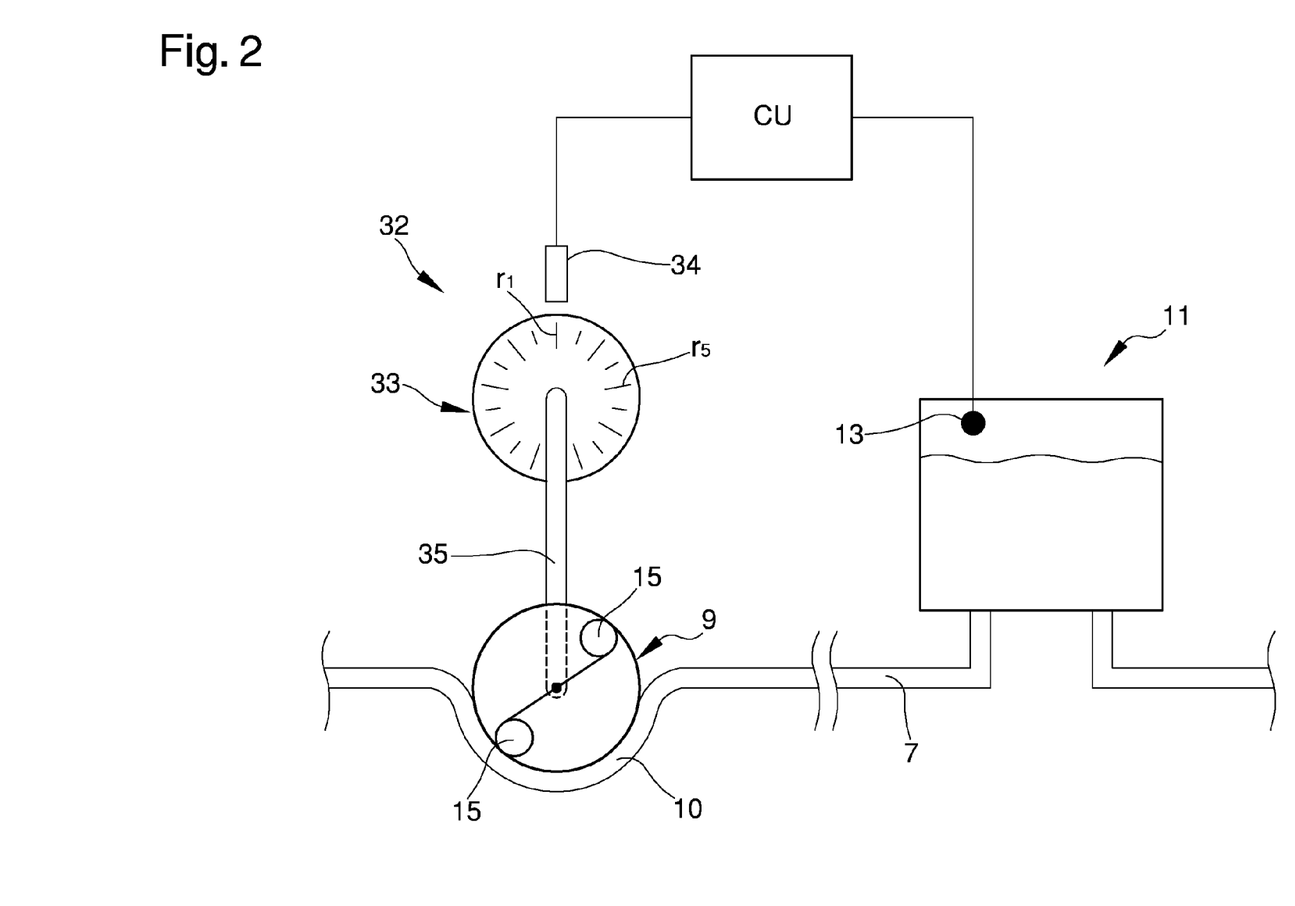
FIG. 2 shows a portion of the apparatus of FIG. 1 in a larger scale.

As it can be seen in FIG. 1, the apparatus 1 comprises at least a first actuator, in the example a blood pump 9, operating at the blood removal line to promote movement of blood removed from the patient "P" from a first end 7a of the removal line 7 connected to the patient "P" towards the first chamber 4. The blood pump 9 is a rotary peristaltic pump, which is active, as shown in FIGS. 1 and 2, on a respective section of tube 10 and able, when moved in a clockwise direction with reference to the figures, to move a blood flow along the removal line 7 towards the first chamber 4 (see the arrows indicating the flow along the line 7).

It should be noted that for the purposes of the present description and the attached claims the terms "upstream" and downstream" can be used with reference to relative positions assumed by components that are a part of or operate on the extracorporeal circuit 2. The terms are understood to mean in reference to a blood flow direction from the first end 7a of the removal line 7 connected to the patient "P" towards the first chamber 4 and thus towards the second end 8a of the return line 8 connected to the vascular access of the patient "P".

In the example of FIG. 1 the extracorporeal circuit 2 comprises at least an arterial expansion chamber 11 operating on the blood removal line 7 of the patient "P" and arranged upstream of the first chamber 4 and upstream of the blood pump 9. The arterial expansion chamber 11 receives blood directly from the patient "P" and accumulates a setting quantity remaining substantially constant during the whole treatment. The extracorporeal circuit comprises at least a venous expansion chamber 12 operating on the blood return line 8 to the patient "P", downstream of the first chamber 4 and upstream of the vascular access which returns the blood to the patient "P".

At least a pressure sensor 13 is configured to detect at least a parameter related to the fluid pressure present in the arterial expansion chamber 11 and a pressure sensor 14 is configured to detect at least a parameter related to the fluid pressure present in the venous expansion chamber 12. In general, the pressure sensors 13, 14 are configured to emit a respective signal corresponding to a measured value of the parameter, and send it to a control unit "CU" on each measurement carried out in successive time instants. Note that it is possible to carry out the detection of the pressure parameter even in close proximity to the arterial or venous expansion chamber 11, 12, for example via a transducer located in either the tube section between the arterial expansion chamber 11 so and the blood pump 9 or in the tract of tube between the arterial expansion chamber 11 and the vascular access to the patient P, or via a transducer located either in the tract of tube between the venous expansion chamber 12 and the return vascular access to the patient "P" or in the tract of tube between the first chamber 3 and the venous expansion chamber 12.

In any case, in a possible adequate positioning of the pressure sensors 13, 14 they act directly in the corresponding arterial and venous expansion chamber 11, 12 at an upper portion thereof where normally (in use) a gas (air) is housed. It is worthy of note that the arterial and venous expansion chambers 11, 12 are in general configured in use and during the treatment to house a predetermined quantity of gas in an upper portion and a predetermined quantity of blood at a predetermined level in a lower portion thereof. Each of the arterial and venous expansion chambers 11, 12 exhibits an inlet for the blood in fluid connection, respectively, with a first part of the removal line 7 connected to the vascular access of the patient "P" and with a portion of the return line downstream of the treatment unit 3. The chambers 11, 12 receive, through the inlet, blood to the chamber itself. In general, the inlets might be positioned at a base portion of the corresponding expansion chamber which is arranged, in use, downwards and is occupied by blood. In an embodiment the inlets can be in connection with a respective internal chamber of the arterial and venous expansion chamber 11, 12 which exhibits a release in the chamber at a predetermined height with respect to the base. Each of the arterial expansion and venous expansion chambers 11, 12 further comprises a respective outlet for the blood in fluid connection with the extracorporeal circuit 2 such as to let, in use, the blood flow out from the chambers. The outlets too are positioned at a base portion of the respective expansion chamber 11, 12 which is arranged, in use, downwards and is occupied by blood.

The portion of removal line 7 which connects the outlet of the arterial expansion chamber 11 to the first chamber 4 of the treatment unit 3 comprises the tract of tube 10 which is engaged by the peristaltic blood pump 9 such as to move, by squeezing the tract of tube 10, the blood in the extracorporeal circuit 2. The particular type of peristaltic pump 9 illustrated is provided with two squeezing bodies (lobes or rollers) 15 such as to act on the tract of tube 10 twice at each rotation of the blood pump 9.

Each of the expansion chambers 11, 12 also exhibits a ventilation opening 16, 17 configured to enable, in use, passage of gas from or towards the expansion chamber 11, 12 for example from or towards the external environment. The apparatus further comprises an actuator 18, 19 for each chamber 11, 12 operating on the ventilation opening 16, 17 (for example on a channel connected thereto) to selectively prevent or enable passage of gas. The ventilation opening 16, 17 is in particular positioned at an upper portion of the expansion chamber 11, 12 which is arranged, in use, upwards, and is occupied by gas. The actuator 18, 19 can be an air pump or also a simple clamp (or another obturator) commanded or not by the control unit "CU" to enable a gas vent in case of need.

In relation to the setting level of blood in the arterial and venous expansion chambers 11, 12, it should be noted that in general the level should be comprised in a range of heights between a minimum value and a maximum value (possibly and in general the minimum value and the maximum value of the venous chamber 12 are different from the maximum and minimum levels of the arterial expansion chamber 11). With the blood level values in the chamber within the above values, we can assume that the apparatus is working in safety conditions; below or above the minimum values, problems of various nature may arise (more fully explained in the following), especially during treatment.

Not least, it is noteworthy that at least one and in general both the arterial and venous expansion chambers 11 and 12 exhibit a constant containing volume, i.e. the chamber is made of a rigid and substantially undeformable material.

The apparatus 1 further comprises a first flow check organ 20, operating on the removal line 7 upstream of the blood pump 9 and the arterial expansion chamber 11 and at least a second check organ 21 of the fluid operating on the blood return line 8 to the patient, downstream of the venous expansion chamber 12. The check organs 20, 21, for example each constituted by a respective clamp commanded by the control unit "CU", are arranged in proximity of the ends 7a, 8a of the respective lines 7, 8 connectable to the patient "P". The apparatus 1 can also comprise an air bubble sensor 22 connected to the control unit "CU" and able to generate a signal which, if above a threshold, determines generation of a closure command of the check organ 21 and possibly a halting of the blood pump 9. The air bubble sensor 22 is in particular located on the blood return line 8 and still more in particular downstream of the venous expansion chamber 12 along the blood flow direction in the extracorporeal body 2.

The blood removal line 7, the arterial expansion chamber 11, the first chamber 4 of the treatment unit 3, the blood return line 8 to the patient "P" and the venous expansion chamber 12 are part of the extracorporeal blood circuit 2 which, during the use of the apparatus 1, circulates blood externally of the body of the treated patient "P".

The apparatus 1 further comprises at least a fluid drainage line 23 connected with an outlet port of the second chamber 5 to receive at least fluid filtered across the semipermeable membrane 6. The drainage line 23 receives the discharge fluid coming from the second chamber 5 of the unit 3, for example, comprising used dialysis liquid and/or liquid ultrafiltered through the membrane 6.

The drainage line 23 leads to a receiving element 24, for example consisting of a collecting bag or a discharge piping of the discharge fluid. One or more dialysate pumps 25 can operate on the drainage line 23. In the figures a single pump is shown by way of example, acting on the drainage line 23. Note that the structure of the drainage line 23 can also be different with respect to what is illustrated (as long as it is able to adequately remove the fluid exiting from the second chamber 5). For example, the drainage line 23 can comprise a single line as shown in the accompanying figures or a main discharge line and an ultrafiltration line which branches out from the main discharge line and which is provided with a respective pump (solution not illustrated).

In the example of FIG. 1 a dialysis line 26 is also present for supplying fresh dialysis fluid for treatment entering the second chamber 5. The presence of the dialysis line 26 is not strictly necessary inasmuch as, in the absence of the line 26, the apparatus 1 is however able to carry out treatments such as ultrafiltration, hemofiltration or plasma filtration.

In a case in which the dialysis line 26 is present, a fluid check organ 27 can be used to selectively enable or prevent fluid passage through the dialysis line 26, depending on whether or not a purification by diffusive effect internally of the treatment unit 3 is planned. The dialysis line 26, if present, is in general provided with a dialysis pump 28 and is able to receive a fresh fluid from a module 29, for example a bag or an on-line preparation section of dialysis liquid, and send the fluid in inlet to the second chamber 5.

Lastly, the apparatus 1 can comprise one or more replacement fluid infusion lines: for example an infusion line 30 can be provided which is connected to the removal line 7 and/or an infusion line 31 connected to the blood return line 8. The pre and/or post-infusion lines 30, 31 can be supplied by appropriate bags or directly by fresh dialysis fluid prepared on-line. The lines are only schematically represented in the accompanying figures.

The apparatus 1 comprises a position sensor 32 associated to the peristaltic pump 9 and configured to enable determining a plurality of reference positions "$pr_1$-$pr_n$" which the peristaltic pump 9 assumes in its cyclic motion.

The illustrated position sensor 32 is a phonic wheel or encoder which comprises a rotor 33 and a pickup 34 or inductive proximity sensor. The rotor 33 of the phonic wheel 32 is solidly constrained to the lobe or roller rotor 15 of the peristaltic pump 9 such as to rotate together with the pump rotor 9. In the accompanying figures, this constraint is schematically illustrated by means of a shaft 35 connecting the two rotors 33, 15. The proximity sensor 34 is mounted fixed on the apparatus 1 and faces towards the rotor 33.

The rotor 33 of the phonic wheel 32 exhibits a plurality of reference signs "$r_1$-$r_n$" (teeth, reliefs, notches) arranged along a circumferential pathway and facing towards the proximity sensor 34. The proximity sensor 34 detects the flow variation of the magnetic field due to the passage of the reference signs "$r_1$-$r_n$". The flow variation generates an alternating pulsating induced current and each of the reference signs "$r_1$-$r_n$" corresponds to a respective pulse.

The control unit "CU" may comprise one or more digital units, for example of the microprocessor type, or one or more analog units, or an appropriate combination of digital and analog units. As illustrated in the example of FIG. 1, the control unit "CU" is connected with the blood peristaltic pump 9 and/or with the dialysate pump 25 and/or with the dialysis pump 28, as well as with pressure sensors 13 and 14 of the arterial and venous expansion chambers 11, 12 and possibly, if present, with auxiliary pressure sensors. The control unit "CU" is further operatively connected with the phonic wheel 32, in particular with the proximity sensor 34. Further, the control unit can be connected to the fluid check organs 20, 21 and, if present, 27. The control unit "CU" is also in communication with the device for detecting bubbles 22, with the module 29 and possibly with the actuators 17 and 18 on the ventilation lines 16 and 17.

The control unit "CU" is configured or programmed to perform the procedures described in the following. In a case in which the control unit "CU" is of the programmable type, this unit is connected to a data support for storing instructions which, when performed by the control unit, determine the execution of the procedures which will be described in the following. The data support can comprise a mass memory, for example optical or magnetic, a reprogrammable memory (EPROM, FLASH) or a memory of another type.

In general, before start of treatment, the apparatus 1 is subjected to a priming procedure controlled by the control unit "CU". In particular, before the treatment a physiological solution is injected into the extracorporeal circuit to wash it and remove any air and residual particles. At the end of this procedure, a setting level of the physiological solution at working pressure is established in the arterial 11 and venous expansion chambers. Once the patient "P" is connected to the apparatus 1 by means of the vascular accesses, the control unit 21 is configured to move at least the blood pump 9 at the start of a treatment in order to create, in the expansion chambers 11, 12, a blood setting level in the lower portion and to confine a complementary quantity of gas in the upper portion, the treatment at this point proceeds for the necessary duration with the aim of appropriately treating the blood removed from the patient "P".

During the whole treatment the blood level in the arterial and venous expansion chamber 11, 12, is continually modified (even if by small values) at least following the fact that the control unit "CU" moves the blood pump 9 in order to generate a variable blood flow comprising a constant flow component at a desired blood flow value and a variable flow component with a substantially nil mean value. This is in particular due to the fact that the blood pump is peristaltic and thus produces a blood flow in the circuit that is not constant, but linked to successive squeezing actions on the tract of tube 10 by the roller's associated to the rotor of the pump 9.

During the treatment it is necessary to monitor and analyse the behaviour of the patient's physiological pressure generators such as the heart and/or the respiratory system. For this purpose, the control unit "CU" is arranged to receive from the pressure sensors 13, 14 located in the respective chambers 11, 12 signals "Ps" indicating the blood pressure in the extracorporeal blood circuit 2. These signals are sampled with a variable sampling frequency that is a function of the rotation velocity of the peristaltic pump 9.

Figure 3:
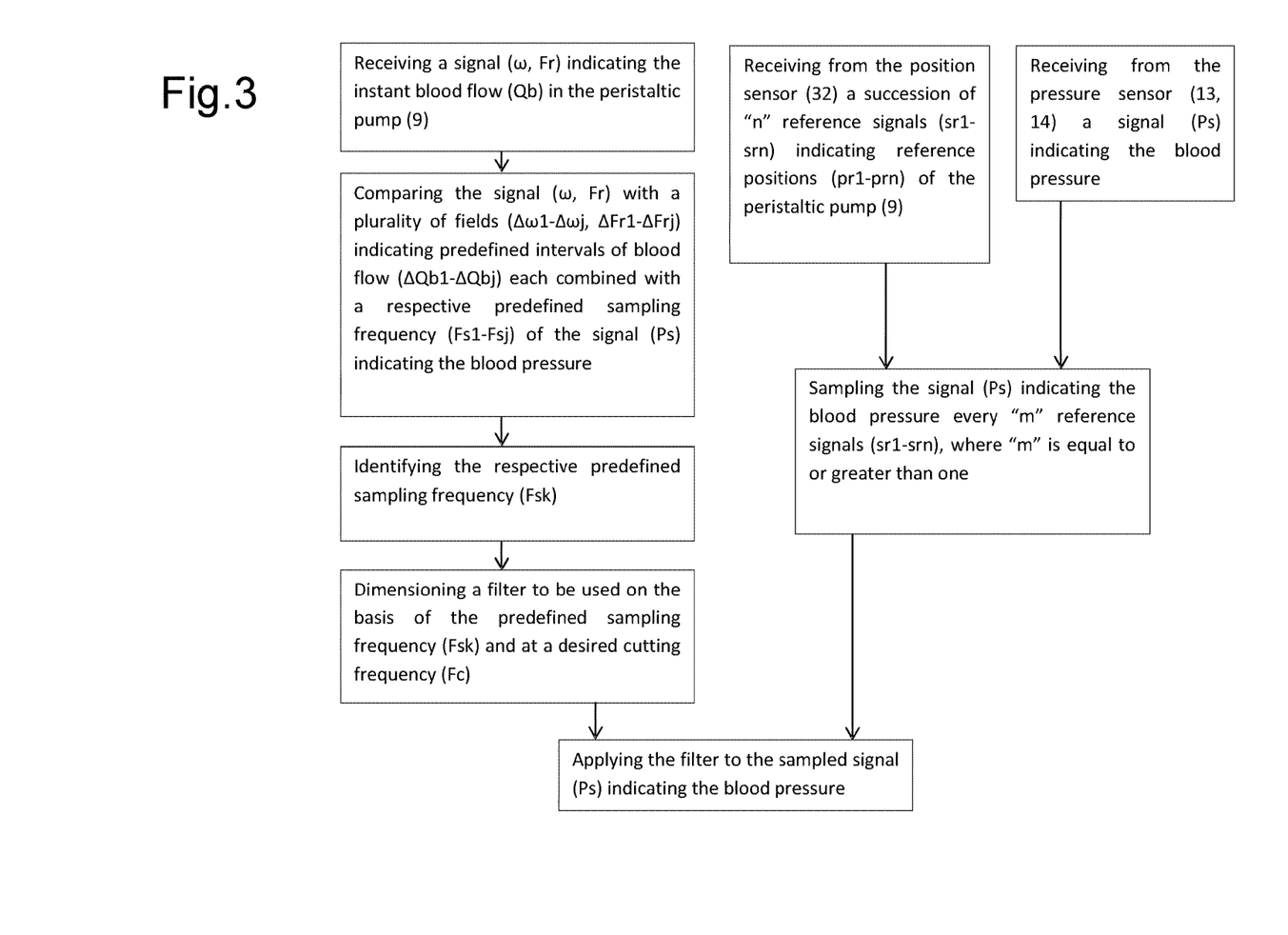
FIG. 3 is a flow chart showing a control procedure according to an aspect of the invention that can be carried out by the control unit of an apparatus for example of the type shown in FIG. 1.

A basic principle implemented by the control unit "CU" and described in the following in detail is detecting/sampling the signal "Ps" indicating the blood pressure from each of the sensors 13, 14 when the peristaltic pump 9 is in a plurality of predefined positions "$pp_1$-$pp_y$". In other words, the instants of detection of the pressure signal coincide with the passage of the peristaltic blood pump 9 through a plurality of predefined positions "$pp_1$-$pp_y$" during the cyclic motion thereof. Therefore the sampling of the pressure signal (or the signals) "Ps" is carried out with a frequency that is not constant but depends on the velocity of the peristaltic blood pump 9.

To this end, the control unit "CU" receives from the proximity sensor 34 a succession of "n" reference signals "$sr_1$-$sr_n$" indicating reference positions "$pr_1$-$pr_n$" of the peristaltic pump 9. Each of these signals "$sr_1$-$sr_n$" is generated by one of the reference signals "$r_1$-$r_n$" located on the rotor 33 of the phonic wheel 32 which rotates, together with the pump 9, in front of the proximity sensor 34. In particular, the signal generated by the proximity sensor 34 is a square wave which defines the angular position of the peristaltic pump 9. Each period of the square wave signal corresponds to one of the reference signals "$sr_1$-$sr_n$" and is equivalent to a rotation of a predetermined number of degrees of the pump 9 axis. For example, the phonic wheel 32 generates a signal with nine hundred and sixty periods per each rotation of the pump 9.

This signal is used as an input for a first counter, which increases, for example, at each rising edge of the signal. A second counter increases at each predetermined time interval (time-based), for example every 2 ms.

The value of the first counter, supplied by the signal of the phonic wheel 32, enables establishing when the peristaltic blood pump 9 has performed a 360° rotation (after nine hundred and sixty periods of the signal). The value of the second counter is read at each complete rotation of the peristaltic blood pump 9, from which the period of rotation of the peristaltic pump 9 is calculated and, consequently, the rotation velocity "w" thereof in [cycles/s] The volume of blood "Sv" moved by the peristaltic pump 9 in a complete cycle in [ml/cycle] is a known datum which depends on the peristaltic pump 9 used.

The instant flow "Qb" of the peristaltic pump 9 in [ml/min] is proportional to the rotation velocity "w" of the pump 9 or to the frequency "Fr" of the reference signals "$sr_1$-$sr_n$" according to the following relations:

$$Qb = \omega \times Sv \times 60 = Fr \times (Sv \times 60)/n$$

By way of example, if Sv=7.65 ml/cycle and w=0.6 cycles/s (which corresponds to an Fr=576 Hz if n=960) then Qb=275 ml/min.

The control unit "CU" further receives, from each of the pressure sensors 13, 14, a respective pressure signal "Ps" and is programmed to detect/sample the signal "Ps" each time the peristaltic pump 9 is in a plurality of predefined positions "$pp_1$-$pp_y$". In other words, the instants of detection of the pressure signal "Ps" coincide with the passage of the peristaltic blood pump 9 through a plurality of predefined positions "$pp_1$-$pp_y$" during the cyclic motion thereof. Thus, the sampling of the pressure signal (or signals) is carried out at a frequency that is not constant but depends on the velocity of the peristaltic blood pump 9.

The predefined positions "$pp_1$-$pp_y$" can match wholly or in part with the reference positions "$pr_1$-$pr_n$". In other words, the reference signals "$sr_1$-$sr_n$" generated in a pump-cycle "n" may all be used to command detection of the signal "Ps" indicating the pressure or one only every "m". If all of them are used, then the reference positions are predefined positions, otherwise only a part of the reference positions are predefined positions. The number "y" so of the predefined positions is the relation "n/m".

For example, one each eight reference signals "$sr_1$-$sr_n$" is used to command detection of the signal "Ps" indicating the pressure, so that:
n=960
m=8
y=120

The sampling frequency "Fs" of the signal "Ps" indicating the pressure is given by the relation Fs=$\omega \times y$=Fr$\times y/n$=Fr/m. If m=1, the sampling frequency "Fs" of the signal "Ps" indicating the pressure matches with the frequency "Fr" of the reference signal "$sr_1$-$sr_n$". In the example in which m=8, the sampling frequency "Fs" of the signal "Ps" is (with w=0.6 cycle/s) equal to 72 Hz.

A further base principle implemented by the control unit "CU" and described in the following in detail is to dimension the filters used for example in order to monitor and analyse the behaviour of the physiological pressure generators of the patient, such as the heart and/or the respiratory system, on the basis of a limited number of predetermined sampling frequencies.

The control unit "CU" is programmed to contain a plurality of fields "$\Delta\omega_1$-$\Delta\omega_j$", "$\Delta Fr_1$-$\Delta Fr_j$" indicating predefined blood flow intervals "$\Delta Qb_1$-$\Delta Qb_j$". In an aspect the predefined intervals of the blood flow "$\Delta Qb_1$-$\Delta Qb_j$" are limited in number, for instance three or four. For instance, the blood flow intervals are three and are as follows: $\Delta Qb_1$=10-265 ml/min; $\Delta Qb_2$=265-335 ml/min; $\Delta Qb_3$=335-580 ml/min. To these intervals correspond (from relations Qb=$\omega \times Sv \times 60$=Fr$\times(Sv\times60)/n$) a same number of cyclic velocity fields ($\Delta\omega_1$=0.022-0.577 cycles/s; $\Delta\omega_2$=0.577-0.73 cycles/s; $\Delta\omega_3$=0.73-1.263 cycles/s) and of reference signal frequencies ($\Delta Fr_1$=20.9-554.2 Hz; $\Delta Fr_2$=554.2-700.6 Hz; $\Delta Fr_3$=700.6-1213.1 Hz). If m=1, the frequency fields of the reference signals ($\Delta Fr_1$; $\Delta Fr_2$; $\Delta Fr_3$) match with sampling frequency fields ($\Delta Fs_1$; $\Delta Fs_2$; $\Delta Fs_3$) of the signal "Ps" indicating the pressure. In the case of the example in which m=8, the following frequency sampling fields correspond to the frequency fields of the reference signals: $\Delta Fs_1$=2.61 69.3 Hz; $\Delta Fs_2$=69.3-87.6 Hz; $\Delta Fs_3$=87.6-151.6 Hz.

The control unit "CU" is programmed to contain, for each of the fields "$\Delta\omega_1$-$\Delta\omega_j$, $Fr_1$-$\Delta Fr_j$" indicating the blood flow intervals "$\Delta Qb_1$-$\Delta Qb_j$" a predefined sampling frequency value "$Fs_k$" of the signal "Ps" indicating the pressure. The predefined sampling frequency "$Fs_k$" for instance corresponds to a reference value "$Qb_k$", for instance to the median value, of the respective blood flow interval "$\Delta Qb_k$".

In the illustrated example, to the first blood flow interval "$\Delta Qb_1$" corresponds a first predefined sampling frequency $Fs_1$=55 Hz (obtained considering a reference flow "$Qb_1$" of 210 ml/min); to the second blood flow interval "$\Delta Qb_2$" corresponds a second predefined sampling frequency $Fs_2$=79 Hz (obtained considering a reference flow "$Qb_2$" of 300 ml/min which is the median value of the respective interval); to the third blood flow interval "$\Delta Qb_3$" corresponds a third predefined sampling frequency $Fs_3$=97 Hz (obtained considering a reference flow "$Qb_3$" of 370 ml/min).

The control unit "CU" compares the instant flow "Qb" of the peristaltic pump 9 with the blood flow intervals "$\Delta Qb_1$-$\Delta Qb_j$" and verifies in which of the intervals the instant flow "Qb" falls. Actually, to perform this flow comparison, the control unit "CU" compares the instant rotation velocity "w" of the pump 9 (or the instant frequency "Fr" of the reference signals "$sr_1$-$sr_n$") with the respective fields "$\Delta \omega_1$-$\Delta \omega_j$" (or $\Delta Fr_1$-$\Delta Fr_1$) and verifies in which of the respective fields "$\Delta \omega_1$-$\Delta \omega_j$" (○ $\Delta Fr_1$-$\Delta Fr_1$) falls.

The control unit "CU" uses the predefined sampling frequency "$Fs_k$" associated to the cyclic velocity field "$\Delta \omega_k$" (among the cyclic velocity fields "$\Delta \omega_1$-$\Delta \omega_j$") in which the instant cyclic velocity "w" falls that corresponds to the instant blood flow "Qb" (or associated to the field "$\Delta Fr_k$" among the frequency fields "$\Delta Fr_1$-$\Delta Fr_j$" of the reference signals "$sr_1$-$sr_n$" in which the frequency "Fr" of the reference signals detected corresponding to the instant blood flow "Qb" falls) in order to dimension the low-pass filter (Anti-Aliasing and/or Noise Suppressor) which is to be used given a desired cutting frequency "Fc".

The Anti-Aliasing and Noise Suppressor filters are applied for instance to the signal "Ps" indicating the blood pressure in the extracorporeal blood circuit 2 in order to extract/isolate the pressure data deriving from the physiological pressure generators with the aim, for example, of monitoring the venous access (VNM) and identifying the dislodgement of the venous needle (VND).

Both the Anti-Aliasing and the Noise Suppressor filters are for instance fourth-order Infinite Impulse Response (IIR) passbands.

In the illustrated example, given a desired cutting frequency "Fc" of 2 Hz, the cutting frequencies "$\omega_c$" expressed in radians of three lowpass filters each combined with one of the three predefined sampling frequencies "$Fs_1$, $Fs_2$, $Fs_3$" are:

1. $\omega_{c1}$=Fc/$Fs_1$=0,226 rad
2. $\omega_{c2}$=Fc/$Fs_2$=0,159 rad
3. $\omega_{c3}$=Fc/$Fs_3$=0,129 rad The pulsation response characterizing each lowpass filter according to the respective cutting frequency "$\omega_{ck}$" is expressed as:

$$h_{lp}[n] = \frac{1}{2\pi} \int_{-\omega_c}^{\omega_c} e^{j\omega n} d\omega$$

$$= \frac{1}{2\pi jn} [e^{j\omega n}]_{-\omega_c}^{\omega_c} = \frac{1}{2\pi jn} (e^{j\omega_c n} - e^{-j\omega_c n})$$

$$= \frac{\sin \omega_c n}{\pi n}, -\infty < n < \infty$$

To sum up, the type of filter is selected among a discrete and small number of filters, each associated to a flow interval "$\Delta Qb_k$" of the peristaltic pump 9 and dimensioned on the basis of the respective sampling frequency "$Fs_k$" so as to have a desired cutting frequency "Fc". According to the measured instant value of the blood flow "Qb", the control unit "CU" uses one of the filters and changes the filter when the instant measured value of the blood flow "Qb" during the treatment falls in a different interval.

Obviously the described methodology is usable in combination with any type of pressure detecting sensor located in the most appropriate points of the extracorporeal blood circuit 2.

While the invention has been described in relation to what is at present considered the preferred and most modern embodiment, the invention is not limited to the described embodiment but, on the contrary, is intended to cover various modifications and equivalent combinations included in the spirit and scope of protection of the appended claims.

The invention claimed is:

1. An apparatus for extracorporeal blood treatment comprising:
    at least a treatment unit having at least a first chamber and at least a second chamber separated from one another by a semi-permeable membrane;
    at least a blood removal line connected to an inlet port of the first chamber and configured to remove blood from a patient;
    at least a blood return line connected to an outlet port from the first chamber and configured to return treated blood to the patient, wherein the blood removal line, the blood return line and the first chamber are part of an extracorporeal blood circuit;
    at least a peristaltic pump operable with the extracorporeal blood circuit to move the blood in the circuit;
    at least a pressure sensor associated to the extracorporeal blood circuit and configured to enable determination of pressure values in said extracorporeal blood circuit;
    at least a fluid drainage line connected to an outlet port of said second chamber; and
    a control unit connected to said at least a pressure sensor and to the peristaltic pump and programmed to:
    move the peristaltic pump with a cyclic motion to generate a blood flow;
    receive from said at least a pressure sensor a signal indicating the pressure of the blood in the extracorporeal blood circuit;
    sample, for each cycle of the peristaltic pump, the signal indicating the blood pressure with a frequency in the time domain depending on the velocity of the peristaltic pump;
    receive a signal indicating the instant blood flow in the peristaltic pump;
    compare the signal with a plurality of fields indicating predefined intervals of blood flow each combined with a respective predefined sampling frequency of the signal indicating the blood pressure;
    identify the field in the plurality of fields to which the signal belongs;
    identify the respective predefined sampling frequency;
    dimension a filter to be used on the basis of the predefined sampling frequency and at a desired cutting frequency; and
    apply the filter to the sampled signal indicative of the blood pressure.

2. The apparatus of claim 1, wherein the signal indicating the blood pressure is sampled when the peristaltic pump is in a plurality of predefined positions.

3. The apparatus of claim 1, comprising at least a position sensor associated to the peristaltic pump and configured to enable determination of positions of the peristaltic pump; wherein the control unit is programmed to carry out the sampling step which comprises:
    receiving from the position sensor a succession of "n" reference signals indicating reference positions of the peristaltic pump;
    sampling the signal indicating the blood pressure every "m" reference signals, where "m" is equal to or greater than one and less than or equal to "n".

4. The apparatus of claim 3, wherein "n" is greater than or equal to fifty.

5. The apparatus of claim 3, wherein "m" is smaller than ten.

6. The apparatus of claim 1, wherein the position sensor comprises a phonic wheel coupled to the peristaltic pump.

7. The apparatus of claim 1, wherein the signal indicating the instant blood flow is a cyclic velocity of the peristaltic pump.

8. The apparatus of claim 7, wherein the cyclic velocity is an average calculated on each cycle of the peristaltic pump.

9. The apparatus of claim 8, wherein the cyclic velocity is calculated by:
   supplying a first counter with the "n" reference signals of the phonic wheel corresponding to a 360° rotation; and
   increasing a second time counter until the first counter reaches the n-th signal;
   considering the inverse of the time used to perform the rotation for obtaining the cyclic velocity in [cycles's].

10. The apparatus of claim 1, wherein the fields indicating the predefined blood flow are cyclic velocity fields.

11. The apparatus of claim 1, wherein the signal indicating the instant blood flow is a frequency of reference signals indicating positions of the peristaltic pump.

12. The apparatus of claim 11, wherein the frequency of the reference signals is an average calculated on each cycle of the peristaltic pump.

13. The apparatus of claim 1, wherein the fields indicating the predefined blood flow intervals are frequency fields of reference signals indicating positions of the peristaltic pump.

14. The apparatus of claim 11, wherein the frequency of the reference signals corresponds to the sampling frequency of the signal indicating the blood pressure or to a multiple of the sampling frequency.

15. The apparatus of claim 13, wherein the frequency of the reference signals corresponds to the sampling frequency of the signal indicating the blood pressure or to a multiple of the sampling frequency.

16. The apparatus of claim 14, wherein the frequency of the reference signals is calculated by:
   supplying a first counter with the reference signals taken into consideration among the reference signals corresponding to a rotation of 360°;
   increasing a second time counter until the first counter reaches the n-th signal;
   dividing the number of reference signals taken into consideration for the time-cycle $\Delta T$ for obtaining the frequency in [l/s].

17. The apparatus of claim 1, wherein each predefined sampling frequency corresponds to a predefined value of the respective predefined interval of blood flow.

18. The apparatus of claim 17, wherein the predefined value is a median value of the respective predefined blood flow interval.

19. The apparatus of claim 1, wherein the number of predefined intervals of blood flow is comprised between two and five.

20. The apparatus of claim 1, wherein the predefined blood flow intervals are comprised between about 0 ml/min and about 600 ml/min.

21. The apparatus of claim 1, wherein the predefined blood flow intervals are comprised between about 10 ml/min and circa 580 ml/min.

22. The apparatus of claim 1, wherein the predefined blood flow intervals are the following: $\Delta Qb1$=10-265 ml/min, $\Delta Qb2$=265-335 ml/min, $\Delta Qb3$=335-580 ml/min.

23. The apparatus of claim 1, wherein each filter combined to a predefined sampling frequency is defined as follows:
   calculating the cutting frequency expressed in radians as $\omega_c = 2\pi \times Fc/Fs$;
   expressing the pulse response which characterizes the low-pass filter according to the cutting frequency as:

$$h_{lp}[n] = \frac{1}{2\pi} \int_{-\omega_c}^{\omega_c} e^{j\omega n} d\omega$$
$$= \frac{1}{2\pi jn} [e^{j\omega n}]_{-\omega_c}^{\omega_c} = \frac{1}{2\pi jn}(e^{j\omega_c n} - e^{-j\omega_c n})$$
$$= \frac{\sin \omega_c n}{\pi n}, -\infty < n < \infty$$

wherein $\omega_c$ is the cutting frequency expressed in radians, Fs is the sampling frequency, Fc is the cutting frequency and $h_{lp}[n]$ is the pulse response.

24. The apparatus of claim 1, wherein the cutting frequency is comprised between about 1 Hz and about 4 Hz.

25. The apparatus of claim 1, wherein the desired cutting frequency is 2 Hz.

26. The apparatus of claim 1, wherein the control unit is configured to extract the pressure data deriving from physiological pressure generators by applying the filter to the sampled signal indicative of the blood pressure.

27. The apparatus of claim 26, wherein the control unit is programmed to monitor the venous access by means of the pressure data deriving from the physiological pressure generators.

28. An apparatus for extracorporeal blood treatment comprising:
   at least a treatment unit having at least a first chamber and at least a second chamber separated from one another by a semi-permeable membrane;
   at least a blood removal line connected to an inlet port of the first chamber and configured to remove blood from a patient;
   at least a blood return line connected to an outlet port from the first chamber and configured to return treated blood to the patient, wherein the blood removal line, the blood return line and the first chamber are part of an extracorporeal blood circuit;
   at least a pump operable with the extracorporeal blood circuit to move the blood in the circuit;
   at least a pressure sensor associated to the extracorporeal blood circuit and configured to enable determination of pressure values in said extracorporeal blood circuit;
   at least a fluid drainage line connected to an outlet port of said second chamber;
   a control unit connected to said at least a pressure sensor and to the pump and programmed to:
   move the pump with a cyclic motion to generate a blood flow;
   receive from said at least a pressure sensor a signal indicating the pressure of the blood in the extracorporeal blood circuit; and
   sample, for each cycle of the pump, the signal indicating the blood pressure with a frequency in the time domain depending on the velocity of the pump; and
   at least a position sensor associated to the pump and configured to enable determination of positions of the pump;

wherein the control unit is programmed to carry out the sampling step which comprises:

receiving from the position sensor a succession of "n" reference signals indicating reference positions of the pump; and sampling the signal indicating the blood pressure every "m" reference signal, where "m" is equal to or greater than one and less than "n".

29. The apparatus of claim 28, wherein the pump is a peristaltic pump and the signal indicating the blood pressure is sampled when the peristaltic pump is in a plurality of predefined positions, and wherein the position sensor comprises a phonic wheel coupled to the pump.

30. The apparatus of claim 28, wherein the control unit is further configured to:

receive a signal indicating the instant blood flow in the peristaltic pump;

compare the signal with a plurality of fields indicating predefined intervals of blood flow each combined with a respective predefined sampling frequency of the signal indicating the blood pressure;

identify the field in the plurality of fields to which the signal belongs;

identify the respective predefined sampling frequency;

dimension a filter to be used on the basis of the predefined sampling frequency and at a desired cutting frequency; and apply the filter to the sampled signal indicative of the blood pressure.

31. The apparatus of claim 28, wherein the signal indicating the instant blood flow is a cyclic velocity of the pump, the cyclic velocity is an average calculated on each cycle of the pump, wherein the cyclic velocity is calculated by:

supplying a first counter with the "n" reference signals of the phonic wheel corresponding to a 360° rotation;

increasing a second time counter until the first counter reaches the n-th signal;

considering the inverse of the time used to perform the rotation for obtaining the cyclic velocity in [cycles's].

32. The apparatus of claim 30, wherein each filter combined to a predefined sampling frequency is defined as follows:

calculating the cutting frequency expressed in radians as $\omega_c = 2\pi \times Fc/Fs$; and expressing the pulse response which characterizes the low-pass filter according to the cutting frequency as:

$$h_{lp}[n] = \frac{1}{2\pi} \int_{-\omega_c}^{\omega_c} e^{j\omega n} d\omega$$

$$= \frac{1}{2\pi jn}[e^{j\omega n}]_{-\omega_c}^{\omega_c} = \frac{1}{2\pi jn}(e^{j\omega_c n} - e^{-j\omega_c n})$$

$$= \frac{\sin\omega_c n}{\pi n}, \quad -\infty < n < \infty$$

wherein $\omega_c$ is the cutting frequency expressed in radians, Fs is the sampling frequency, Fc is the cutting frequency and $h_{lp}[n]$ is the pulse response.

33. The apparatus of claim 30, wherein the control unit is configured to extract the pressure data deriving from physiological pressure generators by applying the filter to the sampled signal indicative of the blood pressure.

34. The apparatus of claim 30, wherein the control unit is programmed to monitor the venous access by means of the pressure data deriving from the physiological pressure generators.

35. The apparatus of claim 28, wherein "n" is greater than or equal to fifty, and wherein "m" is smaller than ten.

* * * * *

UNITED STATES PATENT AND TRADEMARK OFFICE
CERTIFICATE OF CORRECTION

PATENT NO. : 10,124,108 B2
APPLICATION NO. : 14/903478
DATED : November 13, 2018
INVENTOR(S) : David Stefani et al.

It is certified that error appears in the above-identified patent and that said Letters Patent is hereby corrected as shown below:

In the Claims

In Column 17, Line 19 (Claim 9), replace "...the rotation for obtaining the cyclic velocity in [cycle's]." with "...the rotation for obtaining the cyclic velocity in [cycles/s]."

Signed and Sealed this
Fourteenth Day of April, 2020

Andrei Iancu
*Director of the United States Patent and Trademark Office*